(12) United States Patent
Welp

(10) Patent No.: US 7,757,901 B2
(45) Date of Patent: Jul. 20, 2010

(54) MANUALLY OPERATED DISPENSER COMPRISING A PROTECTIVE CAP

(75) Inventor: Gisbert Welp, Sundern (DE)

(73) Assignee: MeadWestvaco Calmar GmbH, Hemer (DE)

( * ) Notice: Subject to any disclaimer, the term of this patent is extended or adjusted under 35 U.S.C. 154(b) by 278 days.

(21) Appl. No.: 11/579,348

(22) PCT Filed: Apr. 26, 2005

(86) PCT No.: PCT/EP2005/004452

§ 371 (c)(1),
(2), (4) Date: Jul. 20, 2007

(87) PCT Pub. No.: WO2005/107838

PCT Pub. Date: Nov. 17, 2005

(65) Prior Publication Data

US 2009/0140008 A1 Jun. 4, 2009

(30) Foreign Application Priority Data

May 3, 2004 (DE) ........................ 10 2004 021 670

(51) Int. Cl.
*B05B 11/00* (2006.01)
(52) U.S. Cl. ............................... 222/321.6; 222/153.13; 222/182; 222/323
(58) Field of Classification Search ............. 222/321.6, 222/321.7, 321.9, 323, 182, 153.13
See application file for complete search history.

(56) References Cited

U.S. PATENT DOCUMENTS

| | | | | |
|---|---|---|---|---|
| 4,944,429 A * | 7/1990 | Bishop et al. | .......... | 222/153.13 |
| 5,257,726 A * | 11/1993 | Graf et al. | ................. | 222/320 |
| 6,173,868 B1 * | 1/2001 | DeJonge | ................. | 222/321.6 |
| 6,257,454 B1 * | 7/2001 | Ritsche | ................. | 222/153.13 |
| 6,297,289 B2 * | 10/2001 | Siff | ............................. | 514/706 |
| 6,386,397 B2 * | 5/2002 | Brotspies et al. | ......... | 222/321.6 |
| 6,964,381 B2 * | 11/2005 | Stradella et al. | ............. | 239/333 |
| 2002/0036207 A1 * | 3/2002 | Ohuo et al. | ................. | 220/830 |
| 2002/0066752 A1 * | 6/2002 | Ritsche et al. | ......... | 222/153.13 |
| 2004/0262339 A1 * | 12/2004 | Stradella | .................... | 222/633 |

FOREIGN PATENT DOCUMENTS

| | | |
|---|---|---|
| BE | 660939 | 7/1965 |
| DE | 29908923 U1 | 7/2000 |
| DE | 69606127 T2 | 9/2000 |
| EP | 1084765 A2 | 3/2001 |
| EP | 1132143 A2 | 9/2001 |
| FR | 2589756 A2 | 5/1987 |
| WO | 03/078963 A2 | 9/2003 |

* cited by examiner

*Primary Examiner*—Kevin P Shaver
*Assistant Examiner*—Donnell Long

(57) ABSTRACT

A manually operated dispenser for flowable media, having a container which has a supply chamber, and a pump head which can be fastened thereto and has a dispensing section with a nozzle-shaped nasal adapter having an outlet opening designed as a spray diffuser, and gripping surfaces protruding laterally from the nasal adapter, and having a protective cap, which has two wings which can be unfolded and are matched in terms of shape, for the nasal adapter, the gripping surfaces having, on opposite sides, end edges which are connected as a single piece to a wing of the protective cap via a respective spring hinge, and the wings have base surfaces which overlap the gripping surfaces.

16 Claims, 2 Drawing Sheets

MANUALLY OPERATED DISPENSER COMPRISING A PROTECTIVE CAP

BACKGROUND OF INVENTION a. Field of Invention

The invention relates to a manually operated dispenser for flowable media, having a container which has a supply chamber, and a pump head which can be fastened thereto.

b. Description of Related Art

EP 1 132 143 A2 discloses a manually operated dispenser comprising a protective cap in order to protect a nasal adapter against soiling or damage while not in use. The protective cap comprises two protective-cap halves which are fastened as wings, which are matched in terms of shape, to the nozzle-shaped dispensing section of the nasal adapter via hinges. In the unfolded state, the wings form gripping surfaces for operating the pump head. A dispenser of this type has the advantage of a slender constructional shape. However, the transmission of the operating pressure via the wings to the pump head makes stable supporting elements necessary, as a result of which the dispenser is heavier and is therefore inevitably less handy.

It is therefore the object of the invention to provide a dispenser which is provided with a protective cap and is handy.

SUMMARY OF THE INVENTION

The invention solves the problems and overcomes the drawbacks and deficiencies of prior art dispensers by providing a dispenser which has a protective cap which can be unfolded and can be folded shut, comprises two protective-cap halves and is fastened captively to the dispenser head. The protective-cap halves, which are designed as wings matched in terms of shape, are connected to the pump head via spring hinges on the end edges of the gripping surfaces. The use of spring hinges not only ensures a long service life but also creates the possibility of providing a lightweight protective cap. In addition, coupling the protective-cap halves to the end edges of the gripping surfaces permits the protective cap to be designed in the form of a covering, which is matched in terms of shape, of an entire head side of a dispenser.

Furthermore, it is advantageous that the protective cap which can be unfolded does not require any substantial change in design of the pump head. The protective cap can simply be attached. The dispensing section and the protective cap may even be injection molded in one part.

The half shells of the protective cap, i.e. the wings, are fixed in an end position by means of the spring hinges. Auxiliary means, such as ribs and the like, can be dispensed with in this respect. A blocking wedge can be provided on the protective-cap halves, which can dip through the gripping part and can deflect a locking pin. The pump head, which can be protected with a closed protective cap, can then also be blockable at the same time.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention and are incorporated in and constitute a part of this specification, illustrate preferred embodiments of the invention and together with the detail description serve to explain the principles of the invention. In the drawings.

DETAILED DESCRIPTION OF THE PREFERRED EMBODIMENTS

Figure 1:
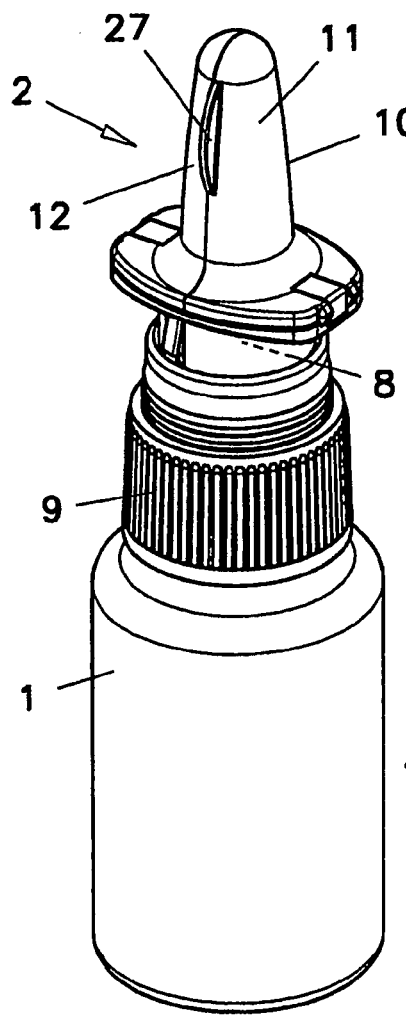
FIG. 1 schematically shows a side view of a dispenser with closed protective cap, FIG. 2 schematically shows a side view of the dispenser with opened protective cap, FIG. 3 schematically shows a top view of the dispenser, FIG. 4 schematically shows a side view of the dispenser with closed protective cap with a subsection in the region of the blocking means.
Figure 2:
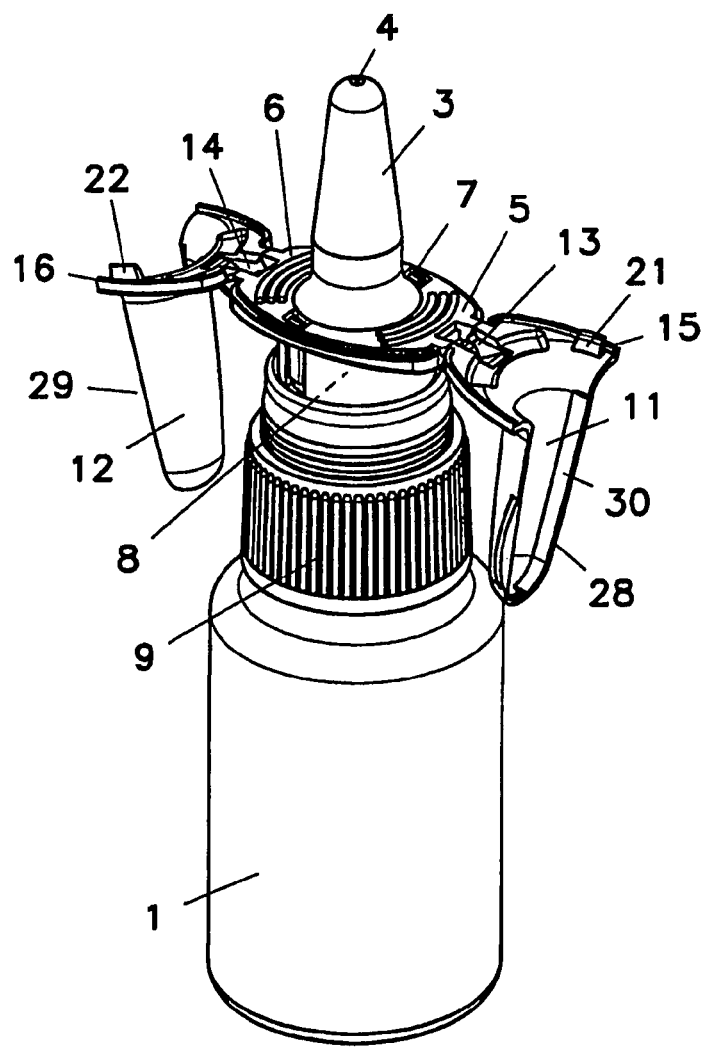

Referring now to the drawings wherein like reference numerals designate corresponding parts throughout the several views, FIGS. 1 and 2 show a manually operated dispenser for flowable media, with a container 1 having a supply chamber and a pump head 2 which can be fastened thereto. The pump head 2 comprises a dispensing section with a nozzle-shaped nasal adapter 3 which has an outlet opening 4 designed as a spray diffuser at the head end. Gripping surfaces 5, 6 protruding laterally from the nasal adapter 3 extend on opposite sides. The gripping surfaces 5, 6 can be connected via a central section 7.

The nasal adapter 3 is assembled to a plunger 8 of a sliding plunger pump 9 which is fastened to the container 1. To dispense a charge in one or more strokes, nasal adapter 3 and container 1 are moved in relation to each other by resting at least one finger on the gripping surfaces 5, 6.

The pump head 2 furthermore comprises a protective cap 10 which comprises two halves and has two wings 11, 12 which can be unfolded and are matched in terms of shape. To fasten the wings 11, 12 to the pump head 2, the gripping surfaces 5, 6 have, on opposite sides, end edges which are connected as a single piece to a wing 11, 12 of the protective cap 10 via a respective spring hinge 13, 14. For this purpose, the wings 11, 12 have base surfaces 15, 16 which cover the gripping surfaces 5, 6 when the protective cap 10 is closed.

The spring hinges 13, 14 permit the wings 11, 12 to be unfolded and to be folded shut, as a result of which the protective cap 10 can be closed and opened. In the opened state, the wings 11, 12 remain connected to the pump head 2, with the result that they cannot be lost. The protective cap 10 is preferably injection molded in one part with the gripping surfaces 5, 6. The protective cap 10 here can be of thin-walled design.

Figure 3:
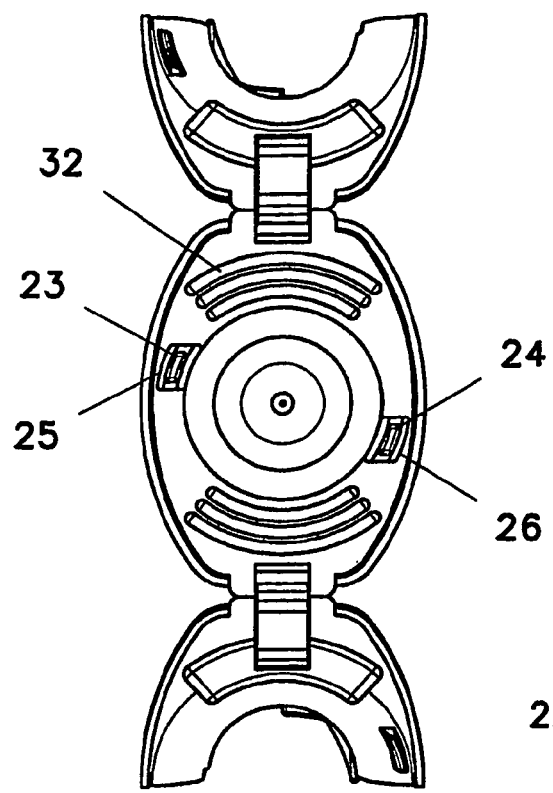
Figure 4:
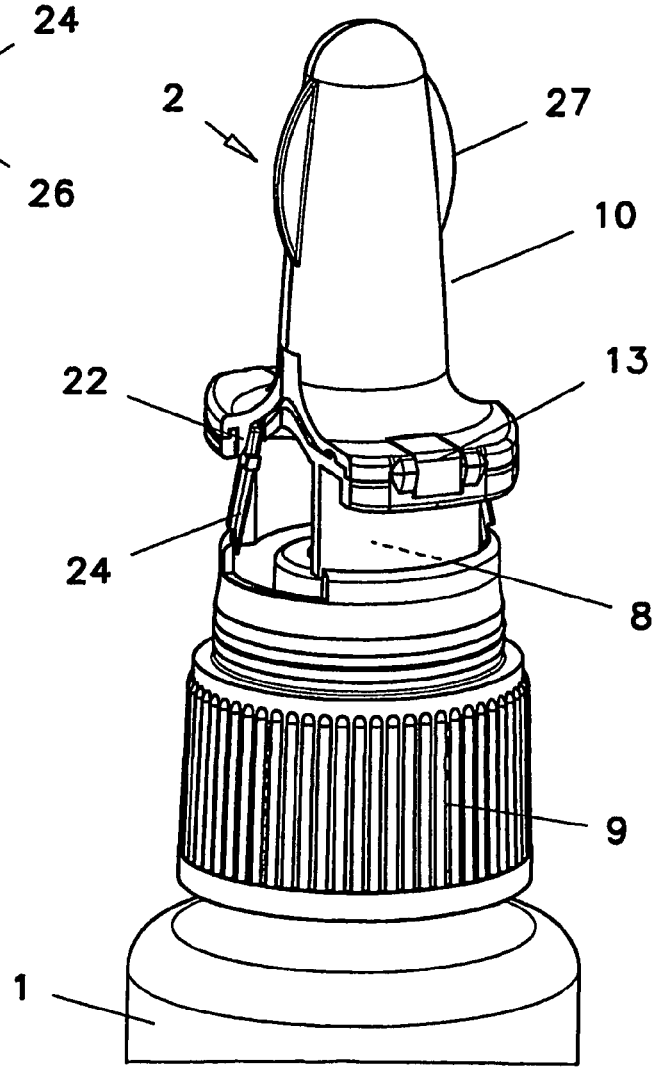

Each wing 11, 12 preferably has a blocking wedge 21, 22 which, with the wings 11, 12 folded shut, i.e. with the protective cap 10 closed, deflect locking pins 23, 24 arranged on the pump head 2 (cf. FIGS. 3 and 4). For this purpose, the blocking wedges 21, 22 dip through recesses 25, 26 in the gripping surfaces 5, 6.

The wings 11, 12 can be fixable in the folded-shut state, for example via a lateral or head-end clip fastener or snap-type fastener 27. Furthermore, the wings 11, 12 can have grooves/springs 30, 31 on the wing bearing surfaces 28, 29 for the aligning engagement in the respectively other wing 11, 12 when the protective cap 10 is closed.

Finally, the gripping surfaces 5, 6 can bear protruding anti-slip elements 32 which, when the protective cap 10 is closed, can dip into recesses in the region of a base surface of the wings 11, 12.

Although particular embodiments of the invention have been described in detail herein with reference to the accompanying drawings, it is to be understood that the invention is not limited to those particular embodiments, and that various changes and modifications may be effected therein by one skilled in the art without departing from the scope or spirit of the invention as defined in the appended claims.

The invention claimed is:

1. A manually operated dispenser for flowable media, having a container which has a supply chamber, and a pump head which can be fastened thereto and has a dispensing section with a nozzle-shaped nasal adapter having an outlet opening designed as a spray diffuser, and gripping surfaces protruding laterally from said nasal adapter, and having a protective cap, which has two wings which can be unfolded and are matched in terms of shape, for the nasal adapter, wherein the gripping surfaces have, on opposite sides, end edges which are connected as a single piece to a wing of the protective cap via a respective spring hinge, and the wings have base surfaces which overlap the gripping surfaces.

2. The manually operated dispenser as claimed in claim 1, wherein the spring hinges are provided for fixing an end position of the wings.

3. The manually operated dispenser as claimed in claim 1, wherein the wings each have a blocking wedge which, with the wings folded shut, deflect locking pins arranged on the pump head.

4. The manually operated dispenser as claimed in claim 1, wherein the wings can be fixed in a folded-shut state via a snap-type fastener.

5. The manually operated dispenser as claimed in claim 1, wherein the gripping surfaces bear protruding anti-slip elements.

6. The manually operated dispenser as claimed in claim 1, wherein the wings have wing bearing surfaces with grooves for aligning engagement in the respectively other wing when the protective cap is closed.

7. A manually operated dispenser for flowable media, having a container which has a supply chamber, and a pump head which can be fastened thereto and has a dispensing section with a nozzle-shaped nasal adapter having an outlet opening designed as a spray diffuser, and gripping surfaces protruding laterally from said nasal adapter, and having a protective cap, which has two wings which can be unfolded and are matched in terms of shape, for the nasal adapter, wherein the gripping surfaces have, on opposite sides, end edges which are connected as a single piece to a wing of the protective cap via a respective spring hinge, and the wings have base surfaces which overlap the gripping surfaces and wherein the wings each have a blocking wedge which, with the wings folded shut, deflect locking pins arranged on the pump head.

8. The manually operated dispenser as claimed in claim 7, wherein the spring hinges are provided for fixing an end position of the wings.

9. The manually operated dispenser as claimed in claim 7, wherein the wings can be fixed in a folded-shut state via a snap-type fastener.

10. The manually operated dispenser as claimed in claim 7, wherein the gripping surfaces bear protruding anti-slip elements.

11. The manually operated dispenser as claimed in claim 7, wherein the wings have wing bearing surfaces with grooves for aligning engagement in the respectively other wing when the protective cap is closed.

12. A manually operated dispenser for flowable media, having a container which has a supply chamber, and a pump head which can be fastened thereto and has a dispensing section with a nozzle-shaped nasal adapter having an outlet opening designed as a spray diffuser, and gripping surfaces protruding laterally from said nasal adapter, and having a protective cap, which has two wings which can be unfolded and are matched in terms of shape, for the nasal adapter, wherein the gripping surfaces have, on opposite sides, end edges which are connected as a single piece to a wing of the protective cap via a respective spring hinge, and the wings have base surfaces which overlap the gripping surfaces and wherein the wings have wing bearing surfaces with grooves for aligning engagement in the respectively other wing when the protective cap is closed.

13. The manually operated dispenser as claimed in claim 12, wherein the spring hinges are provided for fixing an end position of the wings.

14. The manually operated dispenser as claimed in claim 12, wherein the wings each have a blocking wedge which, with the wings folded shut, deflect locking pins arranged on the pump head.

15. The manually operated dispenser as claimed in claim 12, wherein the wings can be fixed in a folded-shut state via a snap-type fastener.

16. The manually operated dispenser as claimed in claim 12, wherein the gripping surfaces bear protruding anti-slip elements.

* * * * *